(12) United States Patent
Cohn et al.

(10) Patent No.: US 12,186,137 B2
(45) Date of Patent: Jan. 7, 2025

(54) METHOD FOR PRECISION PLANNING, GUIDANCE, AND PLACEMENT OF PROBES WITHIN A BODY

(71) Applicant: Ethicon, Inc., Somerville, NJ (US)

(72) Inventors: William Cohn, Houston, TX (US);
Nicolo Garbin, Houston, TX (US);
Emir Kamaric, Houston, TX (US);
Matthew Kuhn, Houston, TX (US);
Ravi Patel, Raynham, MA (US)

(73) Assignee: Ethicon, Inc., Somerville, NJ (US)

( * ) Notice: Subject to any disclaimer, the term of this patent is extended or adjusted under 35 U.S.C. 154(b) by 689 days.

(21) Appl. No.: 16/694,171

(22) Filed: Nov. 25, 2019

(65) Prior Publication Data

US 2021/0153969 A1 May 27, 2021

(51) Int. Cl.
*A61B 90/00* (2016.01)
*A61B 34/10* (2016.01)
(Continued)

(52) U.S. Cl.
CPC ............ *A61B 90/36* (2016.02); *A61B 34/10* (2016.02); *A61B 34/20* (2016.02); *G06T 7/0012* (2013.01); *A61B 2034/101* (2016.02); *A61B 2034/107* (2016.02); *A61B 2034/2055* (2016.02); *A61B 2090/365* (2016.02); *A61B 2090/367* (2016.02);
(Continued)

(58) Field of Classification Search
CPC ......... A61B 90/36; A61B 34/10; A61B 34/20; A61B 2034/101; A61B 2034/107; A61B 2034/2055; A61B 2090/365; A61B 2090/367; A61B 2090/3782; G06T 7/0012; G06T 2207/10081; G06T 2207/10088; G06T 2207/1013
See application file for complete search history.

(56) References Cited

U.S. PATENT DOCUMENTS

| 6,671,538 B1 * | 12/2003 | Ehnholm | A61B 34/20 600/425 |
| 2003/0073901 A1 * | 4/2003 | Simon | A61B 6/547 600/424 |

(Continued)

FOREIGN PATENT DOCUMENTS

WO    WO2019213777 A1    11/2019

OTHER PUBLICATIONS

International Search Report and Written Opinion dated Dec. 23, 2020, from corresponding International Application No. PCT/IB2020/059518 (Year: 2020).*

*Primary Examiner* — Sean D Mattson

(57) ABSTRACT

A method for navigating a probe to a location within a body of a patient, the method comprising visualizing a three-dimensional image of a region of a body of a patient; receiving a selection of a target location within said three-dimensional image of a region of a patient's body; determining and visualizing a preferred pathway for the probe to follow from an external entry point on the patient's body to the target location; visualizing the preferred pathway for the probe simultaneously with an indication of the current actual position of the probe in real time such that the simultaneous visualizations enables a user to align the current actual position of the probe with the preferred pathway; and updating and visualizing an indication of the current actual position of the probe in real time as the probe is advanced to the target location.

44 Claims, 12 Drawing Sheets

(51) Int. Cl.
 *A61B 34/20* (2016.01)
 *G06T 7/00* (2017.01)
(52) U.S. Cl.
 CPC .............. *A61B 2090/3782* (2016.02); *G06T 2207/10081* (2013.01); *G06T 2207/10088* (2013.01); *G06T 2207/10136* (2013.01)

(56) References Cited

U.S. PATENT DOCUMENTS

| | | | | |
|---|---|---|---|---|
| 2003/0220557 | A1* | 11/2003 | Cleary | A61B 34/20 600/409 |
| 2008/0071292 | A1* | 3/2008 | Rich | A61B 90/36 606/130 |
| 2008/0097165 | A1* | 4/2008 | Gattani | A61B 6/12 600/300 |
| 2008/0123921 | A1* | 5/2008 | Gielen | G06T 7/73 382/175 |
| 2009/0149867 | A1 | 6/2009 | Glozman | |
| 2010/0215213 | A1* | 8/2010 | Mielekamp | A61B 34/10 382/103 |
| 2011/0019889 | A1* | 1/2011 | Gering | G06T 7/174 382/131 |
| 2011/0230768 | A1* | 9/2011 | Nir | A61B 8/483 600/461 |
| 2011/0268248 | A1 | 11/2011 | Simon | |
| 2012/0203218 | A1* | 8/2012 | Bonn | A61B 18/1815 250/503.1 |
| 2013/0072784 | A1* | 3/2013 | Velusamy | A61B 18/02 600/424 |
| 2013/0245461 | A1* | 9/2013 | Maier-Hein | A61B 90/361 600/476 |
| 2014/0171792 | A1* | 6/2014 | Dalal | A61B 17/3403 600/424 |
| 2015/0320509 | A1* | 11/2015 | Wei | A61B 34/10 600/424 |
| 2016/0225192 | A1 | 8/2016 | Jones | |
| 2016/0354057 | A1 | 12/2016 | Hansen | |
| 2017/0258526 | A1 | 9/2017 | Lang | |
| 2017/0265943 | A1* | 9/2017 | Sela | A61B 34/20 |
| 2017/0348061 | A1 | 12/2017 | Joshi | |
| 2018/0078316 | A1* | 3/2018 | Schaewe | A61B 34/10 |
| 2018/0132934 | A1 | 5/2018 | van der Weide et al. | |
| 2018/0132944 | A1* | 5/2018 | Yan | G06T 7/74 |
| 2019/0021795 | A1 | 1/2019 | Crawford | |

* cited by examiner

Pre-procedure CT scan

Real-time location

Holographic Overlay

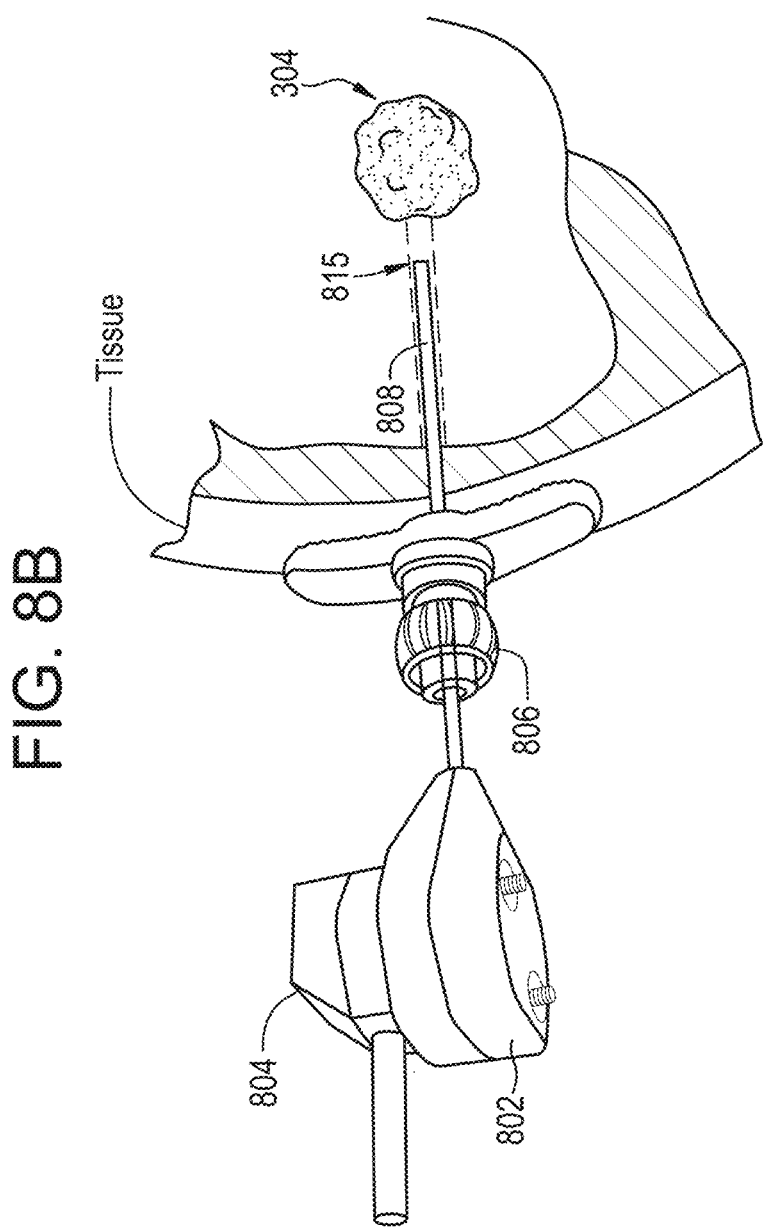

No Acoustic Feedback Before Distance Threshold is Reached

Acoustic Feedback When Distance Threshold is Reached

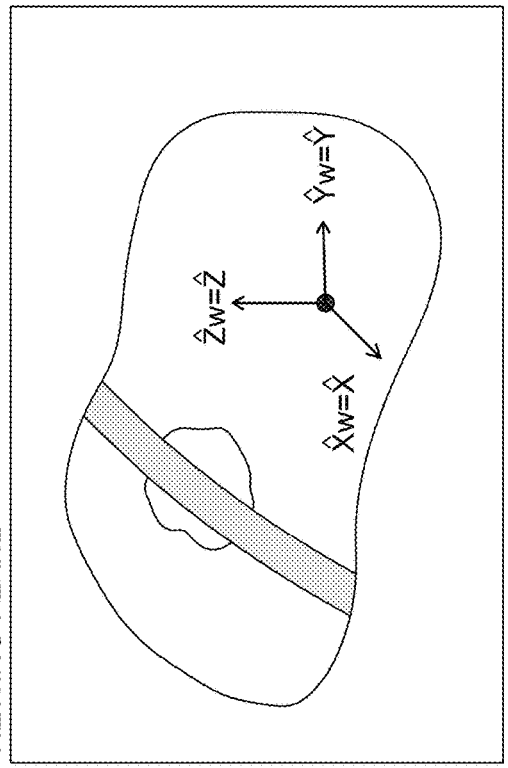

VIEWING PLANE $\alpha = 45 \quad \varphi = 45$

FIG. 11B

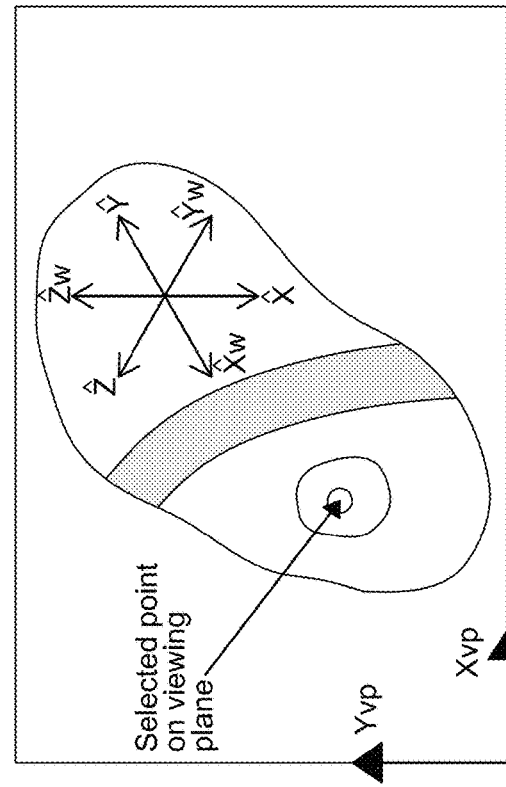

$\alpha \neq 45 \quad \varphi \neq 45$

FIG. 11C

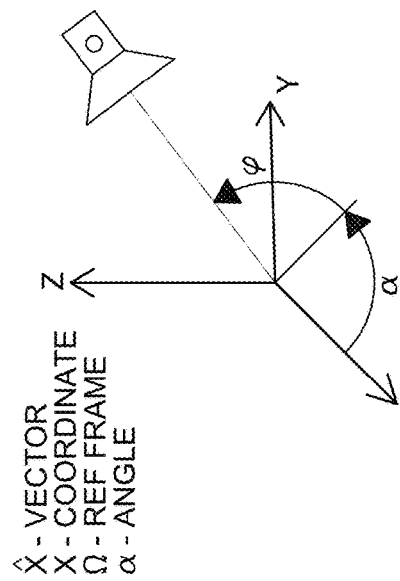

$\hat{X}$ - VECTOR
$X$ - COORDINATE
$\Omega$ - REF FRAME
$\alpha$ - ANGLE $\Omega = [\hat{X}_w \, \hat{Y}_w \, \hat{Z}_w]$ FIXED REF FRAME
$\phantom{\Omega =}$ 3x3

$\Gamma = [\hat{X} \, \hat{Y} \, \hat{Z}]$ MOVING WITH THE CAMERA
$\phantom{\Gamma =}$ 3x3 REF FRAME $\Omega = R(\alpha, \varphi) \Gamma$
$\phantom{\Omega =}$ 3x3

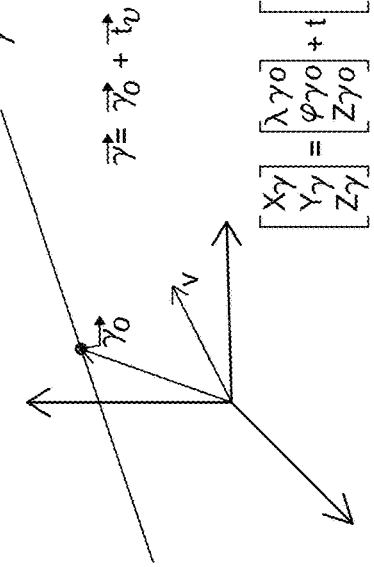

$\vec{\gamma} = \vec{\gamma_0} + \vec{t_v}$ $\begin{bmatrix} X_\gamma \\ Y_\gamma \\ Z_\gamma \end{bmatrix} = \begin{bmatrix} \lambda \gamma_0 \\ \varphi \gamma_0 \\ Z \gamma_0 \end{bmatrix} + t \begin{bmatrix} vx \\ vy \\ vz \end{bmatrix}$

FIG. 11A

METHOD FOR PRECISION PLANNING, GUIDANCE, AND PLACEMENT OF PROBES WITHIN A BODY

BACKGROUND

1. Field of the Disclosure

The present disclosure generally relates to guided navigation of devices such as probes to sites within a body and the system therefor.

2. Discussion of the Related Art

Focal heat destruction or focal hyperthermia is a medically accepted method of treatment for many types of tumors. Focal heat destruction devices may include radiofrequency energy sources, lasers, microwave energy sources, and high-intensity focused ultrasound energy sources. The energy is delivered to the tumors in a minimally invasive manner to achieve tumor destruction without significant damage to the healthy surrounding tissue. The delivery device or probe inserted into the tumor will vary depending on the type of energy source. Long-term survival is achievable with this form of treatment and thus represents a viable alternative to open surgical intervention as well as in cases where tumor removal is not an option.

In radio frequency ablation, electromagnetic energy with frequencies of less than 900 kHz is utilized to generate heat. Radio frequency devices typically operate in the range of between 375 to 500 kHz. In radio frequency ablation, electrode probes are placed within the tumors and alternating high-frequency current displaces molecules within the tumor resulting in localized heating up to about 90 degrees C. In laser ablation, a laser is utilized to deliver infrared light with a wavelength between 800 and 1100 nm to the tumor. The laser light is absorbed by tissue-specific chromophores and photon energy is converted into heat to produce thermal damage to the target tissue. With laser ablation localized heating of between 50 to 100 degrees C. is achievable at the desired power setting for the laser. In microwave ablation, a microwave source, devices capable of generating energy with frequencies greater than or equal to 900 kHz, is utilized to produce electromagnetic radiation that relates to the tumors by an antenna in needle form. This energy produces rapid agitation of the water molecules within the cells of the tumors to cause heating. At the desired power setting, localized heating to temperatures in the range of 60 to 100 degrees C. is achievable. Ultrasound energy may be applied to tumors by extracorporeal or direct needle/probe application for thermal ablation of the tumors. Ultrasound devices at frequencies between 0.8 and 1.6 MHz can deliver narrow focus energy to target tissue after harmlessly passing through soft tissue. This energy is absorbed in the target tissue where it is converted into heat raising the temperature of the tissue at the target site to greater than 80 degrees C. With ultrasound, two mechanisms of action are at work; namely, the thermal energy damage as described above, and mechanical damage due to vibration of the tissue via acoustic cavitation.

What makes this type of therapy effective is cancer cells have an increased sensitivity to heat as compared to normal cells and thus may be destroyed with minimal or no damage to healthy tissue. Damage to the target tissue or tumor occurs in two distinct phases, direct heat injury and indirect injury. Direct thermal injury is determined by the total energy applied to the tumor, tumor biology and tumor microenvironment. Indirect thermal energy occurs after the application of energy has stopped. It is the damage that progresses after the application of energy has ceased. The progressive damage depends on a number of factors including microvascular damage causing endothelial cell damage, ischemia-reperfusion injury, apoptosis or cell death, altered cytokine expression and immune response. All of these progressive factors result in further damage to the cancerous tissue.

As stated above, the survival rates for patients undergoing focal heat destruction rivals those undergoing surgical resection in a significant number of cases; however, reoccurrence of the cancer is much more likely to occur in cases of incomplete destruction of the tumor. In order to completely eradicate a tumor, the entire tumor must be heated to a temperature that will destroy the cells. Accordingly, several factors should preferably be considered. One factor to consider is the size and geometry of the tumor(s). Typically, these procedures are done percutaneously and are thus visualized under fluoroscopy in two-dimensions. CT imaging can be used to view two-dimensions slices of a patient's anatomy and the tumor's geometry; however, compiling these slices to accurately gauge the complex geometry of a given tumor remains a challenge. This may not give the physician an accurate sense of geometry or size. In addition, the probe or probes inserted into the tumor utilizing this method may not be accurately positioned by simply viewing it in two-dimensions. Another factor to consider is the surrounding tissue, including critical anatomy. With two-dimensional imaging, various anatomical features may not be captured. Yet another factor to consider is heat sinking anatomical features. If heat is drawn off the target tissue by surrounding healthy heat sinking tissue, the required temperature to destroy the cancerous tissue may not be achieved. Still yet another factor to consider is electromagnetic wave cancellation. If more than one probe is utilized to radiate the energy, incorrect placement may result in partial or complete phase cancellation. This phase cancellation will result in less energy reaching the target tissue and thus may result in incomplete destruction of the tumor.

Accordingly, improvements are needed.

SUMMARY OF THE DISCLOSURE

The present disclosure relates to a method for navigating a probe to a location within a body of a patient. The method and system of the present disclosure overcomes a number of the limitations associated with the prior art as briefly described above. The method comprising the steps of visualizing a three-dimensional image of a region of a body of a patient, selecting a target location within said three-dimensional image of a region of a patient's body, determining and visualizing a preferred pathway for the probe to follow from an external entry point on the patient's body to the target location, registering the three-dimensional image to the current actual position of the corresponding region of the patient's body, registering the current actual position of the probe to the three-dimensional image and the current actual position of the patient's body, visualizing the calculated preferred pathway for the probe simultaneously with the current actual position of the probe in real time, aligning the current actual position of the probe with the preferred pathway and entry point, advancing the probe into the patient's body along the preferred pathway, and updating and visualizing the alignment of the probe in real time as the probe is advanced until reaching the target location.

In accordance with another aspect, the present disclosure relates to a system for navigating a probe to a location within a body of a patient. The system comprising a three-dimensional image of a region of the body of the patient, a probe configured to be registered to the patient's body position in three-dimensional space, a registration system to register the current actual position of the probe and the patient's body to the three-dimensional image of a region of the body of the patient, an imaging device for capturing real-time images of the region of the body of the patient, a computational machine for calculating a preferred pathway of the probe to a target location within the region of the body of the patient and in communication with the imaging device and registration system, and a display for visualizing the real-time images from the imaging device and the three-dimensional alignment of the current actual position of the probe and the patient's body relative to the preferred pathway and the target location.

BRIEF DESCRIPTION OF THE DRAWINGS

The foregoing and other features and advantages of the disclosure will be apparent from the following, more particular description of preferred embodiments of the disclosure, as illustrated in the accompanying drawings.

FIGS. 8A-8C are diagrammatic representations of the introduction sheath system of the present disclosure.

FIG. 11A-11F show diagrammatic representations relating to example methods for determining a preferred pathway from a three-dimensional image of a region of the body.

DETAILED DESCRIPTION OF THE PREFERRED EMBODIMENTS

Figure 1A:
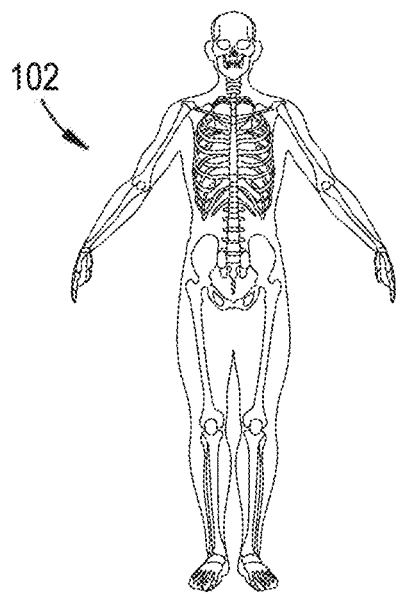
FIGS. 1A-1C are diagrammatic representations of a pre-procedure scan of a patient, the patient and a holographic overlay of the pre-procedure scan overlaid on the patient in accordance with the present disclosure.

Systems and methods are described for navigating a probe to a location within a body of a patient. The probe may comprise a needle, introducer, catheter, stylet, or sheath. Other probes may be used. Methods may comprise visualizing a three-dimensional image of a region of a body of a patient. As an example, the three-dimensional image of a region of a body of a patient may be based on one or more of magnetic resonance imaging (MRI), computer tomography (CT), or ultrasound. Other imaging techniques may be used. Methods may comprise receiving a selection of a target location within said three-dimensional image of a region of a patient's body. As an example, the receiving a selection of a target location is via interaction with a display device configured to output one or more of the visualizing steps. Other inputs may be used to effect selection. Methods may comprise determining and visualizing a preferred pathway for the probe to follow from an external entry point on the patient's body to the target location. The preferred pathway may be determined by transforming a selected point in a two-dimensional view of the three-dimensional image of a region of a body of a patient into a line (e.g., line of sight) through the three-dimensional image of a region of a body of a patient. Methods may further comprise calibrating the preferred pathway to compensate for shift of anatomical structures pre-operatively. Alternatively or additionally, methods may further comprise calibrating the preferred pathway to compensate for shift of anatomical structures intra-operatively. Methods may comprise registering the three-dimensional image to the current actual position of the corresponding region of the patient's body. Methods may comprise registering the current actual position of the probe to the three-dimensional image and the current actual position of the patient's body. Methods may further comprise updating the registration of the three-dimensional image to the patient to compensate for shift of anatomical structures. Methods may comprise visualizing the preferred pathway for the probe simultaneously with an indication of the current actual position of the probe in real time such that the simultaneous visualizations enables a user to align the current actual position of the probe with the preferred pathway. As an example, the indication of the current actual position of the probe comprises the position of the probe in three-dimensional space. As a further example, the indication of the current actual position of the probe comprises the projected extension of the probe in three-dimensional space. Methods may comprise updating and visualizing an indication of the current actual position of the probe in real time as the probe is advanced to the target location. Additionally, output of an auditory or visual feedback may be used to warn the user about information regarding proximity to the target location and/or to warn the user about information regarding proximity to critical anatomical structures.

Ablation of anatomical material such as tumors is used herein as an illustrative example. Other processes and procedures may benefit from the systems and methods as described herein. Focal heat destruction or ablation is an important therapeutic strategy for treating certain tissues such as benign and malignant tumors. As set forth above, there are a number of energy sources that may be utilized, and each has its advantages and disadvantages. Radio frequency ablation is widely utilized and there are a number of radio frequency-based devices and power supplies that are currently utilized. However, radio frequency energy has several limitations, including the rapid dissipation of energy in surface tissues resulting in shallow "burns" and failure to access deeper tumor tissues. Another limitation associated with radio frequency ablation systems is the tendency of eschar (slough) and clot formation to form on the energy emitting electrodes which in turn limits the further deposition of energy.

Given the limitations associated with radio frequency ablation, microwave ablation offers a viable and effective alternative. More specifically, microwave energy provides for deeper tissue penetration, an insensitivity to charring, a lack of necessity for grounding, more reliable energy deposition, faster tissue heating and the capability to produce much larger thermal lesions than radio frequency ablation. There are a number of devices that utilize electromagnetic energy in the microwave frequency range as a means for focal heat destruction or ablation.

The present disclosure relates to a method and system for navigating one or more probes to a location within a body of a patient. The present disclosure relates to a method of and associated system for determining an accurate three-dimensional model of a tumor and its surrounding environment, inclusive of anatomical structures, as well as a means for automatically calculating the number of energy radiating probes and their respective positioning/trajectory specifics of the energy radiating probes within the tumor(s) to ensure no destructive interference of the radiating energy in the patient and the complete eradication of the targeted cancerous cells. To achieve optimal trajectories for each probe utilized to ensure complete tumor destruction, the methodology of the present disclosure includes predictive analytics which account for the effects of tissue shrinkage due to electro-magnetic radiation exposure. Although, as set forth above, there are several energy sources available, exemplary embodiments of the present disclosure will be described with respect to a system for the delivery of microwave radiation as a means for focal heat destruction. An exemplary system is described in United States Patent Publication Number 2018/0132934, assigned to NeuWave Medical, Inc.

As an illustrative example, optimum trajectories of probes (e.g., ablation probes or other probe devices), which may be determined (e.g., calculated) based upon anatomical geometry obtained from a variety of pre-procedural imaging modalities, including magnetic resonance imaging (MRI), computer tomography (CT) and ultrasound, may be calibrated to the patient in real-time to account for internal shifting of anatomical structures within the body between the time of imaging and the time at which the patient is prepped and positioned on the operating or procedure table.

A a further example, calibration maybe accomplished by mapping the pre-procedural imaging, for example, CT scans, and the predetermined directional surgical path vectors that indicate the determined optimum trajectories of the probes through the body onto the patient via anatomical markers, vision systems, and/or markers placed onto the patient's body. Similar processes are utilized in numerous procedures, for example, guided sinus surgery utilizing masks. The location and orientation of the surgical path vector as well as the anatomical features (e.g., tumor(s)) of interest may then verified using, for example, an ultrasound probe in real-time.

As an illustrative example, once this is accomplished, the physician, an artificial intelligence (AI) module of the software implementing the methodology of the present disclosure in conjunction with an ablation system, and/or the physician guided by the AI may then tag and record discrete slices of the tumor and the surgical path vector as the fan beam of the ultrasound probe is passed across the both the surgical path vector and the full target tumor. As the ultrasound records the position of the tumor and other relevant anatomical structures in the surrounding space, the AI/software automatically adjusts the CT-overlay to match the patient's real-time anatomy via a three-dimensional, line-of-best fit optimization, and subsequently adjusts the optimized surgical path vector for ablation probe trajectories to account for any anatomical shifting that may have occurred since the initial formulation of the trajectories that may have been based on historical imaging data. The ablation system described herein may also incorporate an augmented reality (AR) headset through which the physician could visualize a "holographic" CT scan that is overlaid onto the patient, thereby allowing the physician to visualize the three-dimensional geometry of the tumor in space, i.e. as if the physician was peering directly into the patient's body, as well as the orientation of the optimized surgical path vector for ablation probe trajectories.

In addition, the probe(s), patient, and ultrasound probe are outfitted with three-dimensional position tracking sensors that all cross-communicate with each other much like the equipment used in conjunction with the Carto® 3 System available from Biosense® Webster, Inc. a Johnson & Johnson Company. The system is configured to guide the physicians in their placement of the ablation probes by verifying the ablation probes are positioned correctly, in real-time, as they are advanced into the patient. The equipment could be tracked visually using IR markers placed on the probes, ultrasound, and AR headset or through other means.

Figure 1B:
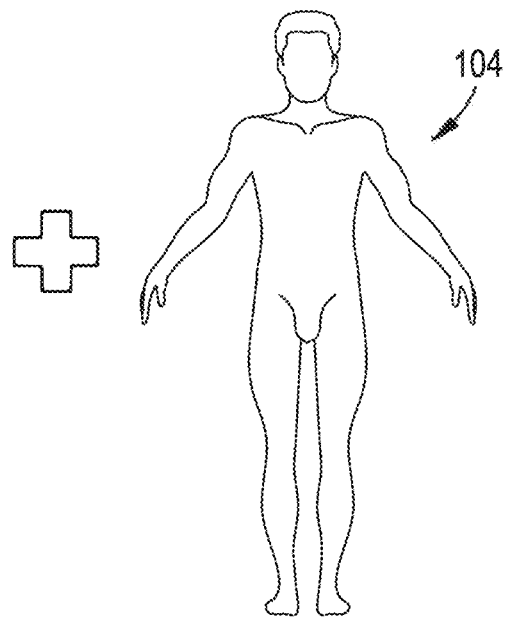
Figure 1C:
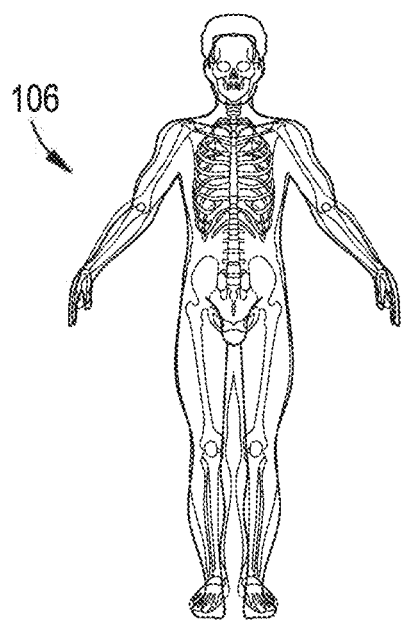

A detailed description of each step in the process is given below. In order to best illustrate and describe the process, a tumor in the liver of a patient will be utilized (FIG. 2); however, it is important to note that this is only for exemplary purposes and the process may be utilized anywhere in the body. The first step in the process is to scan the patient with a CT at the time of the procedure or gather the data from a historical scan and use the information captured in the scan to model the tumor and the surrounding tissue and anatomical structures in the region of potential ablation probe insertion and energy dissipation. The CT scan described herein captures the relevant data relative to the tumor and surrounding structures; namely, blood vessels, including the vena cava, the aorta, the hepatic artery, the portal vein, the hepatic vein, and organs such as the spleen when working in or proximate the liver. Referring to FIGS. 1A-1C, there is illustrated a holographic overlay of a patient's pre-procedure scan on the actual patient as seen through an AR headset or other suitable display device. It is understood that various display devices may be used. As a non-limiting example, a display device such as an AR headset aids the physician in visualization and instrument alignment with ablation probe trajectories as well as tumor location in three-dimensional space. However, other displays may provide similar functionality.

A pre-procedure scan, for example a CT scan 102 with the registration markers and a transmitter (reference location of the markers and transmitter are chosen for demonstration purposes, additional locations are able to be used for this step of the procedure), is taken and input into display device. A more detailed description of the registration markers is given subsequently with respect to FIG. 1D. As an illustrative example, when implementing AR technology, when the physician views the actual patient 104 in the procedure room while wearing the AR headset. He or she will see the holographic overlay 106 of the pre-procedure scan 102 on the patient 104, which as explained in greater detail herein allows for the initial steps in the precision guidance of the one or more probes. As described herein, various display devices may be used.

A CT scan is a computerized x-ray imaging procedure which may be utilized to generate a three-dimensional image of a patient that shows the skeleton, organs, blood vessels and tissue as well as any abnormalities present such as tumors. A CT scanner or CT machine utilizes a narrow beam of x-rays which are rotated around the body of the patient to provide signals that are processed by the scanner's microprocessor to generate cross-sectional images or slices of the body. After a number of successive slices are collected by the microprocessor, they are stacked and compiled together to form a three-dimensional image of the patient relative to the scanned region. Accordingly, the images produced by the scanner can be viewed as individual slices, two-dimensional images or three-dimensional images. What makes the CT scan so valuable as a diagnostic tool also makes it a valuable element in the present disclosure; namely, the data collected may be parsed or utilized in various ways. For example, various components of an image may be isolated and then viewed relative to other portions of the patient as is explained in greater detail subsequently.

As set forth herein, a key to the present disclosure is the protection of the tissue and non-harmful anatomical structures surrounding the tumor while achieving complete destruction of the targeted tumor(s). In order to accomplish this, the precise anatomy of the tumor and surrounding structures must be determined. The CT scan of the patient includes all of the data necessary or required to model the patient's anatomy, including the tumor. Once the CT scan is taken, the data associated with the tumor may be isolated from the data associated with the surrounding tissue by having the software searching for any material in a particular density range. This is possible because each tissue type has a particular density and the software of the present disclosure is cable of isolating tumor cells from normal cells. By isolating this data and using it to create a highly precise three-dimensional model, the physician will be able to visualize the full entirety of a target anatomical structure or feature (e.g., tumor) and proceed with the disclosure described in this description, for example, to fully ablate the tumor based on the calculations of the algorithm for the number of ablation probes to utilize, ablation probe trajectories and placement and energy delivered by each ablation probe. In this manner, all tumor cells may be destroyed without damaging surrounding tissue and/or anatomical structures. Once again it is important to note that other functions that require probes or probe like devices may be utilized in accordance with the present disclosure.

Once the tumor is modeled and overlaid relative to the rest of the necessary or required anatomical structures of the patient, the ablation probe positioning, quantity, and trajectory are calculated by the physician by providing the ability to navigate the model in search of the best trajectory regions to avoid healthy tissues/regions, or a combination of the aforementioned. In this manner, complete destruction of the tumor may be achieved with minimal damage to the surrounding tissue and organs. Relative to efficiency, the determination of adequate positioning of the ablation probe(s) within the tumor may involve considerations of the ablation energy dissipation profiles, which may be affected by proximate heat sinks, the volumetric size of the tumor, the potential number of paths providing safe trajectories leading into the tumor, and the intensity of the ablation energy when utilizing the probe. By doing so, the disclosure is more efficient in energy utilization and safety. Additionally or alternatively, blood flow in the region of the anatomical feature (e.g., tumor) may also be modelled by the computational geometry algorithm and ablation probe energy and placement may be optimized to account for this blood flow.

After initial trajectory/positioning determination of the ablation probe(s), the CT scan of the patient as described above with respect to FIGS. 1A-1C must be registered to the patient at the time of the actual procedure as part of the process of the present disclosure. Physically attached or anatomically structured markers are utilized to register the CT scan with the actual patient. Typically, there are any number of anatomical markers that may be utilized in the registration process if said path is chosen. For example, skeletal structures or landmarks may be utilized. In addition, surface structures such as nipples may also be utilized. Essentially, any fixed structure on or in the body may be utilized to register the CT scan to the patient. With the CT scan registered to the patient at the time of procedure, the next step in the process may involve compensation for anatomical shifts within the patient once the patient is positioned for the procedure and from the any shifts that may have occurred if historical CT data was used for the generation of the 3D models and paths, as opposed to one created the day of the procedure. Anatomical shifts may be caused for any number of reasons during the time between the initial scan that was utilized to create the 3D models and the paths and to the timepoint of the ablation procedure. It may be as simple as patient placement on the procedure platform. An additional CT scan taken at the time of the procedure or a real-time ultrasound may be utilized to generate a more accurate image of the desired region or portion of the patient that the target was determined to rest in.

Additionally or alternatively, if the tumor(s) or any of the surrounding tissues, organs and/or blood vessels did move, the CT scan/ultrasound will be used with the algorithm and the software to measure the shift and the computational geometry algorithm will automatically calculate new ablation probe trajectories as well as any other relevant ablation probe information or said action may be achieved by the physician if desired. More specifically, as set forth above, the updated CT/ultrasound records the position of the tumor and other relevant anatomical structures in space, the AI/algorithm has the ability to automatically adjust the CT overlay to match the patient's real-time anatomy via a three-dimensional, line-of-best fit optimization, and subsequently adjusts the optimized ablation probe trajectories.

Once the final trajectories for the ablation probes are calculated, as well as other relevant ablation probe information, the one or more ablation probe introduction sheaths have to be registered to the patient/model. There are a number of suitable ways to gather the information to register the ablation probes to the patient, including optical registration, for example, utilizing IR cameras or sensors, or through precision mapping techniques using technology similar to the Carto® 3 System available from Biosense® Webster, Inc. a Johnson & Johnson Company which utilizes electromagnets to generate magnetic fields through which the ablation probes may be registered. As set forth above, an exemplary ablation probe may be part of the system described in United States Patent Publication Number 2018/0132934, assigned to NeuWave Medical, Inc. The introduction sheaths are to be interchangeable with the ablation probes that are to be used to deliver the energy as well as any necessary tools inclusive of the introduction stylet that is used prior to the insertion of the ablation probe. This introduction sheath is necessary for the ongoing swap from the introduction stylet to the ablation probe. The introduction sheath is the element of the disclosure that is marked and tracked in space relative to the transmitter. The receiver gives indication for where the surgical path trajectories are when utilizing the introduction sleeve with either the introduction stylet, ablation probe, or similar item. However, with that being said, the receiver may be attached to any item of known geometry for the purpose of spatial tracking.

After registration of the ablation probe guides has been completed, all relevant trajectories are to be accounted for in the virtual model and the software with the overlaid ultrasound via the present disclosure. The ultrasound image itself is to be overlaid with the ablation probe sheath specific trajectories. These trajectories not only include the location of the ablation probe/introduction stylet in the patient relative to all the tumor(s), but also the projected location of the ablation probe/introduction stylet if the user is to advance down with a controlled linear path.

The relevant trajectories are to be used in the next stage when it comes to real-time verification of the calculated ablation probe trajectories utilizing ultrasound. The ultrasound image is overlaid with all necessary trajectories, which may be toggled on/off to narrow down to one specific trajectory at a time. The ultrasound is then utilized to scan the region of interest to verify that minimal anatomical structures are damaged all the way through the full length of the ablation probe path. In addition, a verification of the termination of said path is verifiable at the tumor site, where the path is to directly intersect the structure at the predetermined location within the tumor.

After the verification of the calculated path or trajectory is completed, the entry point is located on the patient via the introduction sheath with the introduction stylet/ablation probe attached, a calibrated tool, or a tool with a receiver attached to it with a known location in the virtual coordinate system. The entry point is the beginning of the calculated ablation probe path with respect to the highest level of intact material for the patient, typically the skin.

A potential sequence of ablation probe insertion to site of ablation is described in detail subsequently. Once the entry point is located, the introduction sheath with the introduction stylet is then positioned at the entry point. Live ultrasound verification may be used at this step and every succeeding step to follow for confirmation of ablation path deviation, if any. With real-time verification of where the introduction stylet or ablation probe are in the patient's body, the introduction stylet or the ablation probe may be inserted while having an overlaid graphical representation of the pre-planned and verified surgical path all the way to the ablation site of the tumor. In addition to visual verification of the ablation probe location in the body relative to its target tumor and surrounding anatomical structures, and audible sound or additional feedback may be incorporated to provide a second sense for location relative to the target end-point and the tumor itself. Additionally or alternatively, at this stage, the energy levels and duration are all calculated and determined based on the tumor itself and the type of ablation probe used, which the algorithm will calculate.

To summarize the process of the present disclosure at this juncture, the geometry of the tumor and the modelling of the surrounding tissue, organs and blood vessels provide information to the physician for determination of a preferred trajectory for introduction of the ablation probe(s) into the body with minimal risk of damaging critical structures and in order to achieve compete destruction of the tumor. The CT scan may be registered to the patient and when the patient is positioned for the procedure, an ultrasound image or an additional CT scan may be utilized to determine if any and compensate for any anatomical shifting and this information is used to automatically recalculate ablation probe information. As an illustrative example, this can be achieved by placing markers (e.g., markers 152 (FIG. 1)) on the patient body, prior to the CT scan to determine a pre-operative reference frame. Intraoperatively, the same markers, now present in the CT data set, can be localized in the operative space via a dedicated localization tool to generate the intra-operative reference frame. By overlapping the two defined frames is possible to register the actual patient anatomies over the digitized ones. Other registration mechanisms may be used.

Once the CT scan is registered to the patient, the one or more ablation probes are then registered to the patient. Once the one or more ablation probes are registered to the anatomy of the patient, they may be inserted or introduced into the patient by the physician along the calculated trajectories. The one or more ablation probes may be equipped with guidance systems such as overlaid virtual paths displayed on the screen of the ultrasound, the projected path of the probe itself, and the location of the probe in space to ensure that the ablation probes are following along the calculated trajectories to the proper position for tumor destruction. The present disclosure described herein may be equipped with an acoustic system to aid in ablation probe positioning relative to the targeted ablation site. In addition, the ablation probe(s) and ultrasound probe, are outfitted with three-dimensional position tracking sensors that cross-communicate with each other.

Figure 1D:
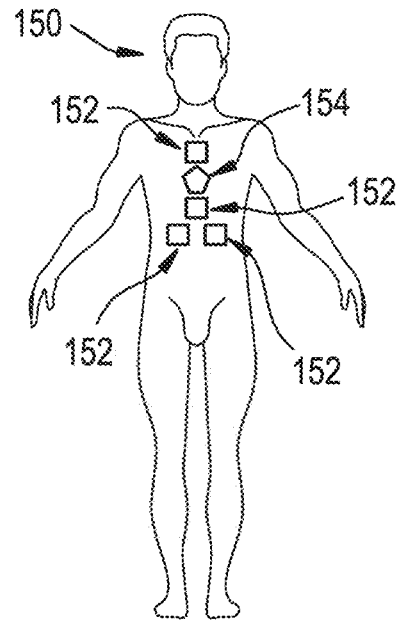
FIG. 1D is a diagrammatic representation of registration markers on a patient and an image of a patient with the registration markers in accordance with the present disclosure.
Figure 2:
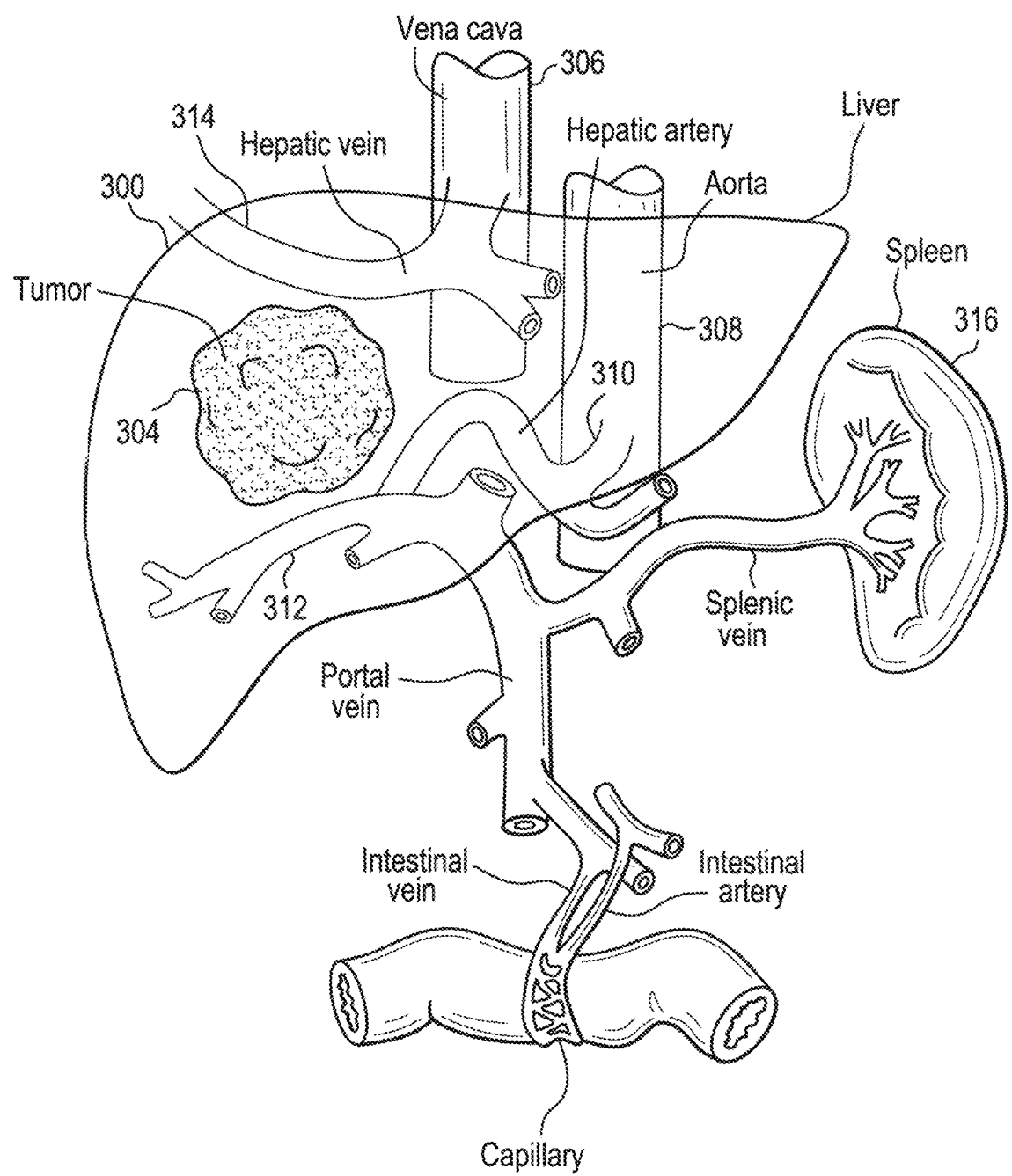
FIG. 2 is a diagrammatic representation of a human liver with a tumor and surrounding anatomical structures.
Figure 3A:
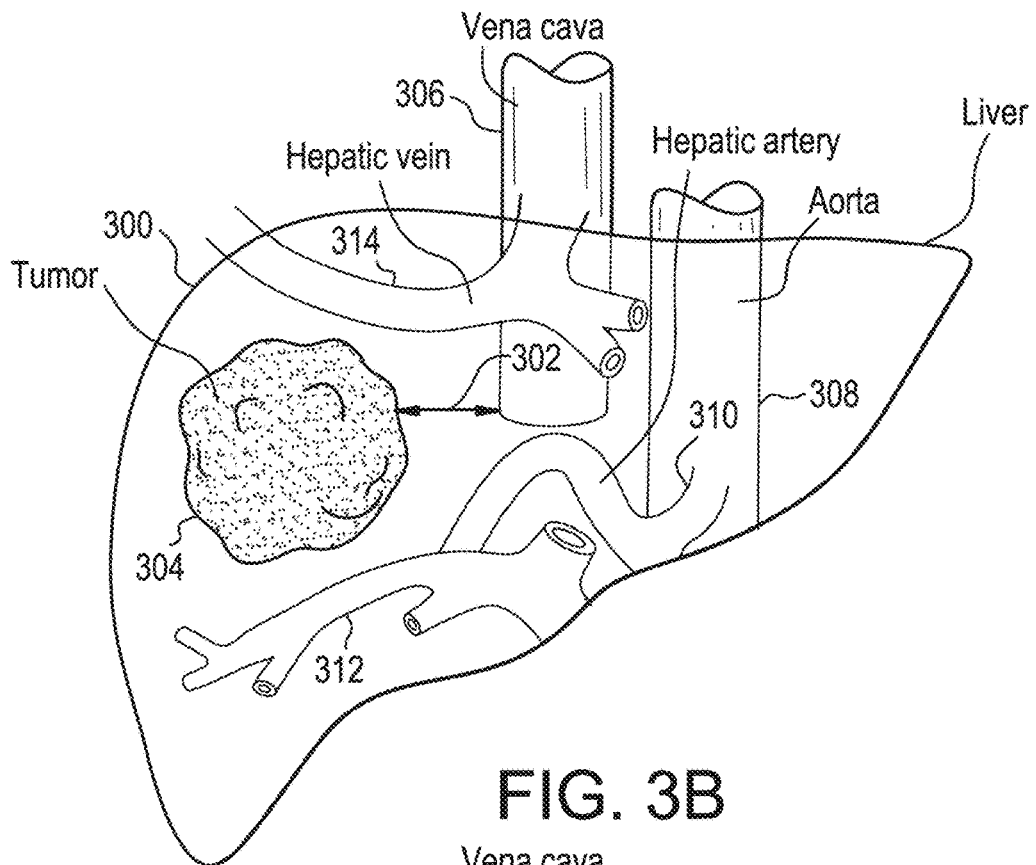
FIG. 3A is a diagrammatic representation of the human liver with a tumor of FIG. 2 at a first time associated with an initial scan in accordance with the present disclosure.
Figure 3B:
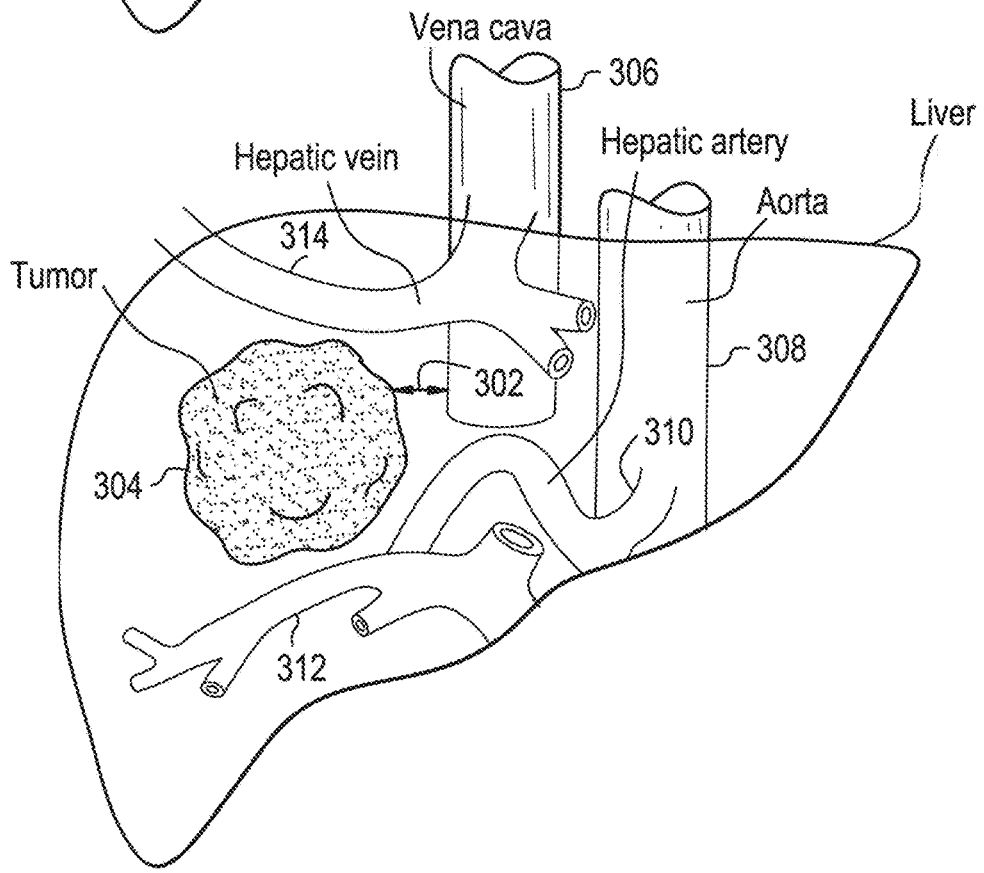
FIG. 3B is a diagrammatic representation of the human liver with a tumor of FIG. 2 at a second time associated with a second scan in accordance with the present disclosure.

Referring now to FIG. 2, there is illustrated a diagrammatic representation of a human liver 300 and surrounding anatomical structures. As shown, there is a tumor 304 in the liver 300. The CT scan described herein captures the relevant data relative to the tumor 304 and surrounding structures; namely, blood vessels, including the vena cava 306, the aorta 308, the hepatic artery 310, the portal vein 312, the hepatic vein 314, and organs such as the spleen 316. Additionally or alternatively, the computational geometry algorithm calculates the required information for tumor ablation based on all this collected data. The CT scan and the resultant analysis done by the user, shows the proximity of the tumor(s) to other organs and blood vessels for the reasons set forth herein. FIG. 3A is a detailed diagrammatic representation of the tumor 304 at the time of the initial CT scan and FIG. 3B is a detailed diagrammatic representation captured by the ultrasound or the additional CT scan. As is illustrated, the tumor 304 has shifted position in some manner and to some degree due to anatomical shifting. As illustrated in FIGS. 3A and 3B, the distance between the vena cava 306 and the tumor 304 has shifted in space by some distance represented by arrow 302. In FIG. 3B, the tumor 304 is closer to the vena cava 306 and thus new trajectories for the one or more ablation probes may be required due to the proximity to a major blood vessel and its heat sink effect. As an illustrative example, a computational geometry algorithm automatically recalculates a new trajectory for the one or more ablation probes. The algorithm compares the scans with the use of multiple registration markers 152 and a transmitter 154 positioned at specified known locations on or proximate the patient 150, as illustrated in FIG. 1D.

Figure 4:
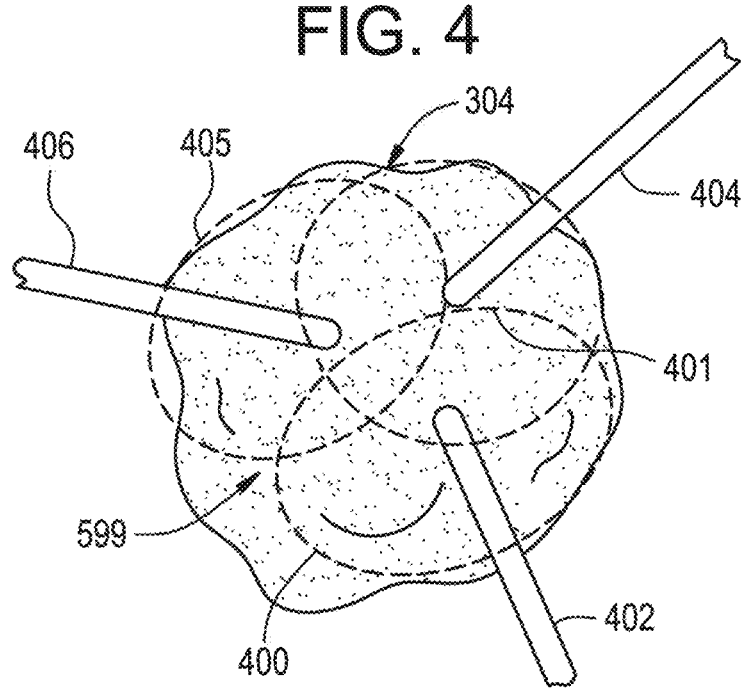
FIG. 4 is a diagrammatic representation of multiple ablation probes and associated ablation regions within a tumor.

FIG. 4 illustrates the use of multiple ablation probes; namely, ablation probe one 402, ablation probe two 404, and ablation probe three 406 for the ablation of the tumor 304 based on the volumetric burn region, ablation region one 401, ablation region two 403, and ablation region three 405 of each of the ablation probes inserted into the tumor 304. It is important to note that three probes were chosen here for exemplary purposes. Typically, the probes would be introduced in a somewhat parallel fashion and not from completely different directions as illustrated for ease of explanation. A number of factors described herein determine the number of probes to be utilized as well as their trajectories. With the variation in the target's volumetric size and location within the body, multiple probes as shown in this figure would be utilized to provide the target with the needed ablation to cover the regions of the tumor. As an illustrative example, this may be completed by the system being capable of calculating the region of burn for each ablation probe depending on its location within the tumor relative to intensity of the energy delivery, size of the ablation probe, nearby heat sinks, and other general factors.

Figure 5:
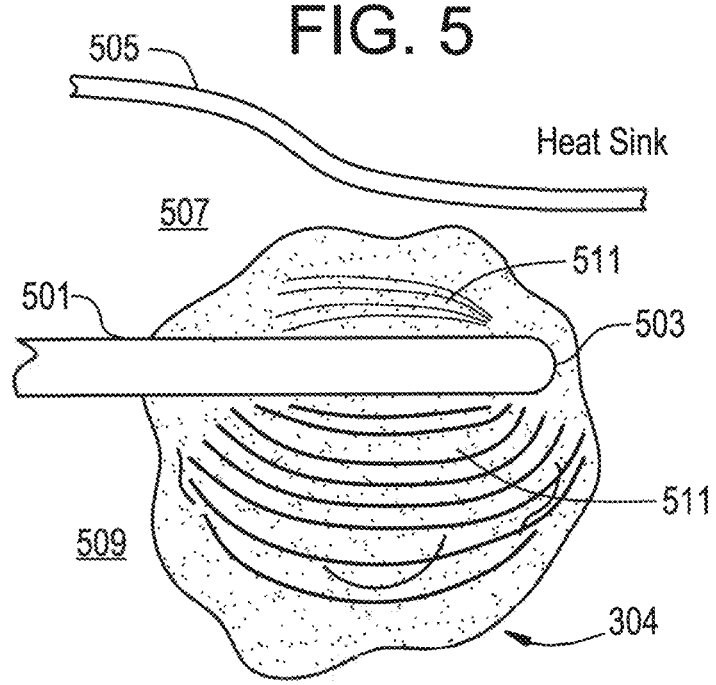
FIG. 5 is a diagrammatic representation of the heat sink effect for an ablation probe within a tumor.

FIG. 5 illustrates the aforementioned heat sink effects for the ablation probe when in the tumor 304. For exemplary reasons, a single, simple ablation probe 501 is illustrated in the image. It is important to note that any suitable type of probe may be utilized whereas an ablation probe is one such example. As shown in the figure, the ablation energy delivery region or distal tip 503 of the ablation probe 501 is within some region of the tumor 304. There is a nearby major blood vessel 505 that provides a heat sink effect for that region of tissue and thus should be avoided. As a non-limiting example, the system within the disclosure described herein may utilize an algorithm to predict the modified burn regions with respect to heat sink regions 507 and non-heat sink regions 509. As such, the system is able to predict/calculate the regions of burn 511 with respect to specific ablation probes used.

Figure 6A:
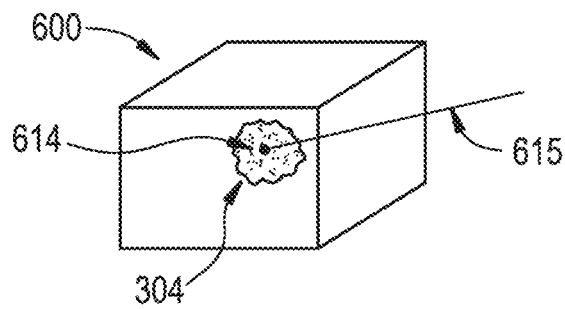
FIG. 6A is diagrammatic representations of a single ablation probe trajectory in accordance with the present disclosure.
Figure 6B:
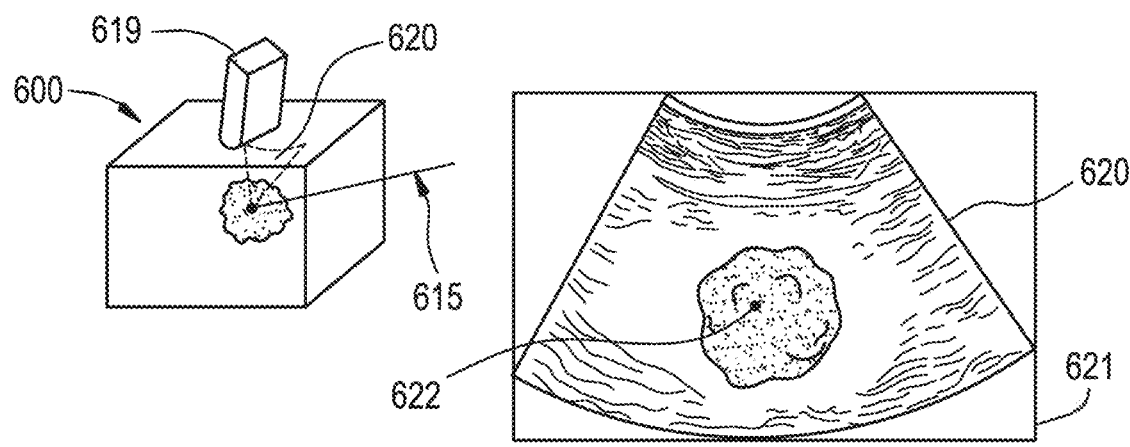
FIGS. 6B and 6C are diagrammatic representations of the methods of visualization for the calculated path of FIG. 6A in accordance with the present disclosure.
Figure 6C:
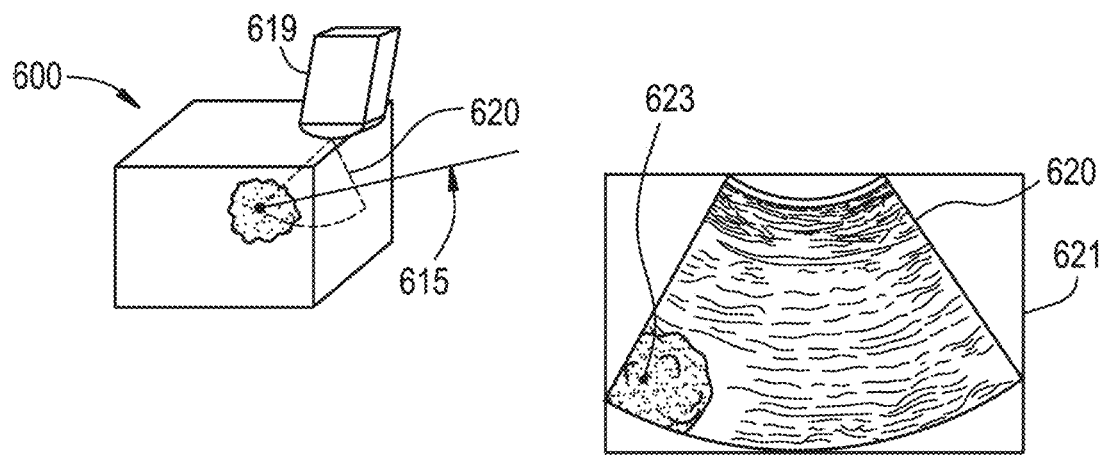

FIG. 6A illustrates a single calculated trajectory to the site of ablation in the tumor (e.g., based on the computational geometry algorithm). Although reference is made to ablation of a tumor other probes and procedures may benefit from the systems and methods described herein. In the figure, the determined (e.g., calculated) trajectory 615 to the center 614 of the tumor 304 along the predetermined path is seen beginning at the surface of the virtual patient 600 and ending in the ablation site within the tumor 304. The system itself is designed to allow for the real-time monitoring of the calculated path or trajectory 615 with an ultrasound 619 device illustrated in FIGS. 6B and 6C. FIGS. 6B and 6C illustrate the method of visualization for the calculated path or trajectory 615 relative to different ultrasound orientations; namely, perpendicular to the calculated path or trajectory 615 or along the calculated path or trajectory 615. In FIG. 6B, the ultrasound device 619 is oriented perpendicular to the calculated path or trajectory 615, creating an ultrasound slice 620 at some depth of the calculated path or trajectory 615. The resulting ultrasound image 621 has the overlaid calculated path or trajectory 615 shown as the perpendicular cross-section of a customizable shape, object, or image 622. In FIG. 6C, the ultrasound device 619 is oriented along the directional axis of the calculated path 615, creating an ultrasound slice 620 along a larger portion of the calculated path or trajectory 615, if not all of it. The resulting image 621 has the overlaid calculated path trajectory 615 shown as an in-line axial cross-section of the customizable shape, object, or image 623. In addition to the calculated path or trajectory 615 overlaid on the ultrasound image 621, the projected trajectory as well as the actual location of the ablation probe in real-time are also tracked on the image.

Figure 7:
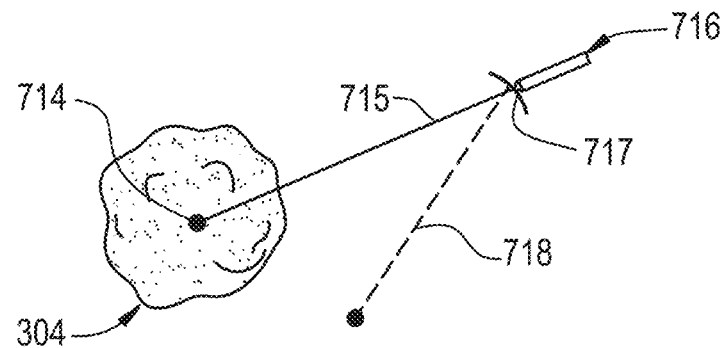
FIG. 7 is a diagrammatic representation of a calculated trajectory projection based on real-time location of the ablation probe in accordance with the present disclosure.

FIG. 7 illustrates point 717 as an example entry point for a probe 716. A calculated trajectory projection 718 may be determined based on the real-time location of the ablation probe 716 at the time of the procedure or during planning studies. The calculated trajectory projection 718 may be projected line calculated based on the angulation and location of the real-time ablation probe 716. As shown, the calculated trajectory projection 718 may be overlaid on an image such as an ultrasound image (e.g., image 621 in FIGS. 6B and 6C) to allow a user to visualize a projection of the calculated trajectory of the probe 716. In this example, the calculated trajectory projection 718 is shown missing the ablation site 714 which is the center of the tumor 304. Thus, a user may determine that based on the calculated trajectory projection 718, correction is necessary. As a further example, a planned trajectory 715 may be calculated and overlaid on the image to allow a user to compare the planned trajectory 715 with the calculated trajectory projection 718 and to make adjustments based on the same. As an illustrative example, a user may align the calculated trajectory projection 718 with the planned trajectory 715 in order to follow the planned path to a particular location (e.g., the ablation site 714). In addition to the projection 718, the projection or trajectory item (or other elements in display) may changes colors or some significant element of its item when the ultrasound is creating a sliced image over the actual ablation probe 716. This additional indicator may aid the user in knowing the real-time location of the ablation probe 716 during any planning or insertion steps. All of the calculated trajectories, both pre-planned and real-time trajectories, all may be displayed on the a display device such as a screen or a visualization headset in addition to being represented in the overlaid ultrasound image.

At the stage of ablation probe insertion, the following figures are used to describe a potential series of steps that can be taken to get the ablation probe to the calculated zone/point. It is important to note that this is not the only series of steps that can be taken for this portion of the procedure.

Figure 8A:
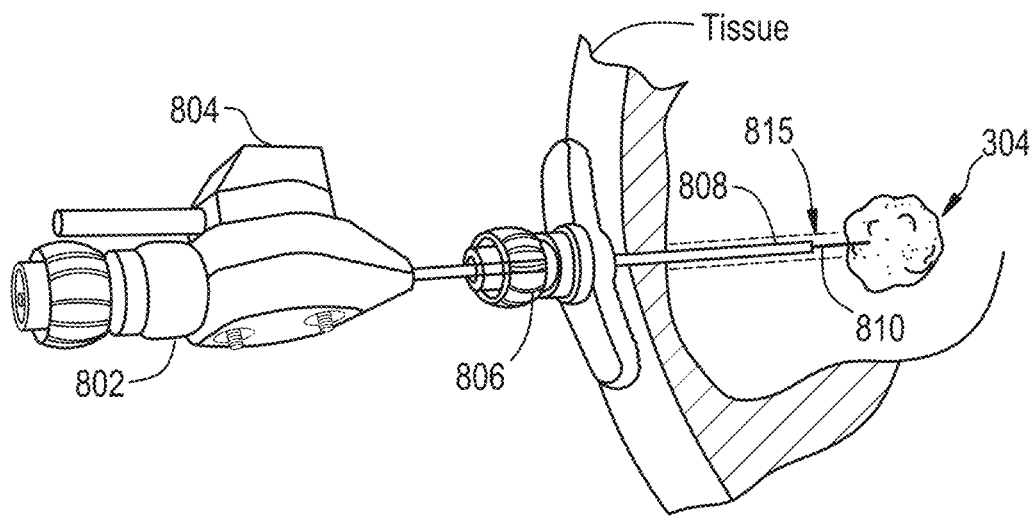
Figure 8C:
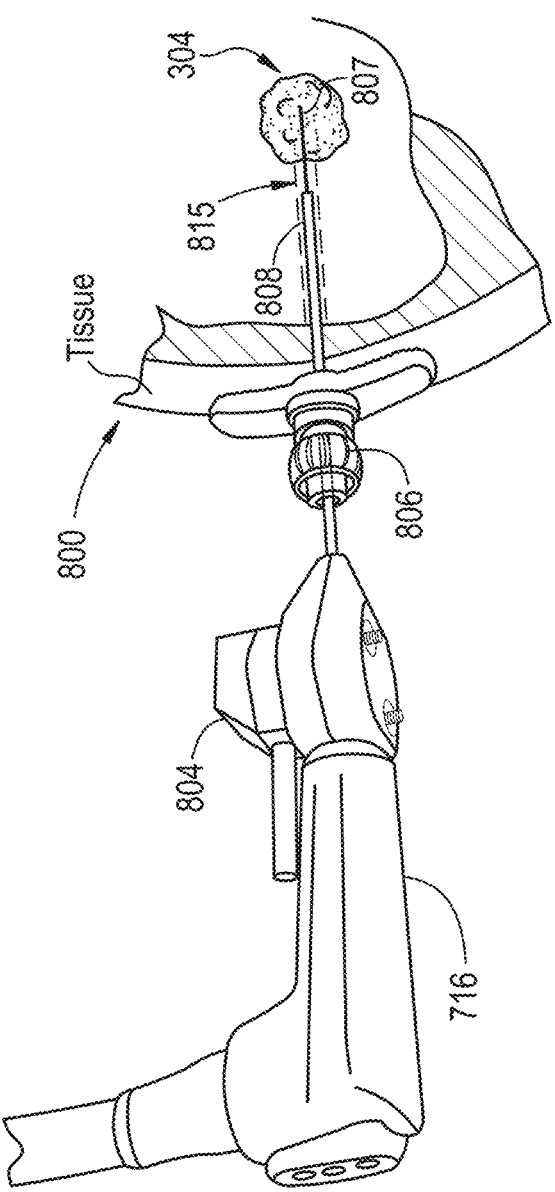

FIG. 8A illustrates the introduction sheath system inclusive of its introduction sheath handle 802, receiver 804, introduction sheath locking mechanism 806, and the introduction sheath 808 itself. This system can be used as the initial insertion, where the introduction stylet 810 is used in place of the ablation probe 716 all the way to the site of ablation at the tumor 304 along the pre-determined surgical path 815. Its position is tracked and utilized for all of the imaging and calculations with the use of the receiver 804. Once the introduction stylet 810 reaches the calculated depth and location, the introduction sheath locking mechanism 806 is engaged to lock that location in space relative to the patient and its respective body. FIG. 8B moves onto the next stage of the ablation probe 716 insertion process, by removing the introduction stylet 810 from the overall assembly. This opens up the connection point 802 that has the ability to mate with multiple parts, in this figure, the introduction sheath 808 is shown resting before the tumor 304, due to the introduction stylet 810 and the ablation probe 716 having the same geometries resulting in the same end offset location in the tumor 304. Again, that location being the calculated one from the software. FIG. 8C now brings in the actual ablation probe 716 insertion into the already set path and location created by the introduction stylet 810. As shown with the tip 807 of the ablation probe 716, it is exactly at the same terminal point that the introduction stylet 810 was at, and where the calculated site of ablation is based on the software. As a non-limiting example, software of the present disclosure may determine the optimal placement and energy emitted by each probe to ensure no interference between probes. A more detailed description of the ablation probe may be found in US Patent Publication 2018/0132934. It is important to note; however, that any suitable ablation probe may be utilized in accordance with the present disclosure.

Figure 9:
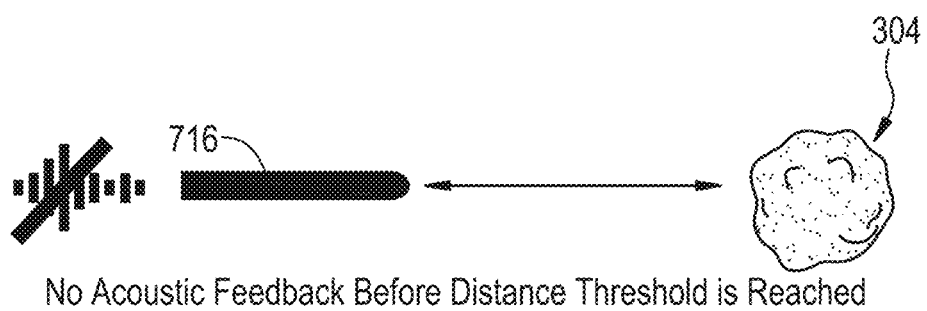
FIG. 9 is a diagrammatic representation of an exemplary feedback mechanism in accordance with the present disclosure.
Figure 9:
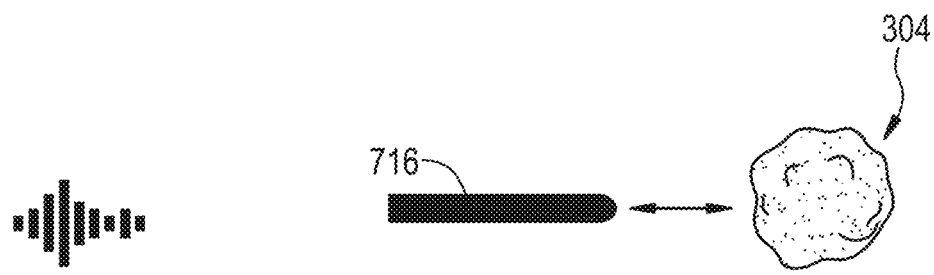

FIG. 9 illustrates the acoustic feedback or similar/non-similar mechanism used for proximity to tumor feedback. For the acoustic example, as the introduction stylet 810, ablation probe 716, or similar item approaches the tumor 304 (FIGS. 8A, 8B and 8C) the user is presented with a specified sound and pitch or increasing occurrence or modification of said items. This will ensure the user is aware of the location of the introduction stylet 810, ablation probe 716, or similar item with respect to the target in addition to just the visual cues.

Figure 10:
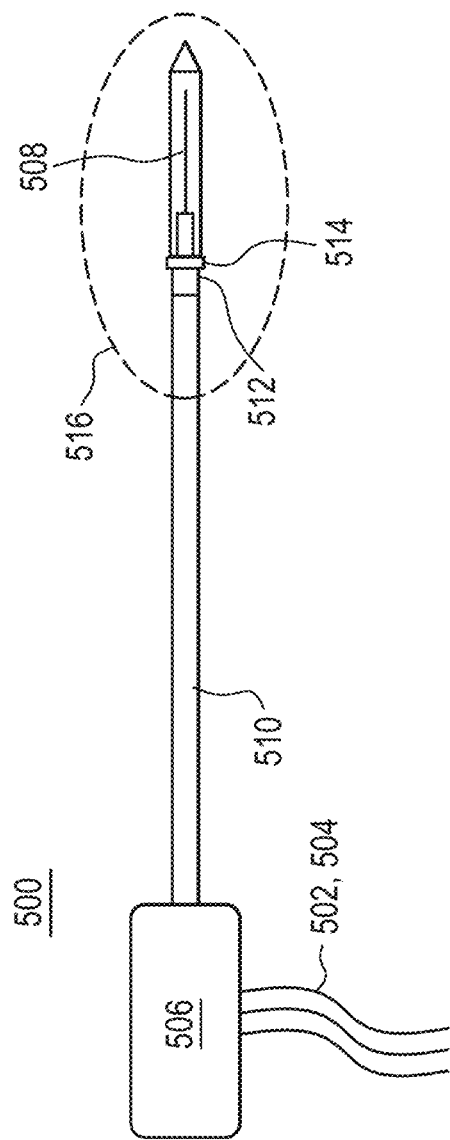
FIG. 10 is a diagrammatic representation of an exemplary ablation probe in accordance with the present disclosure.
Figure 11D:
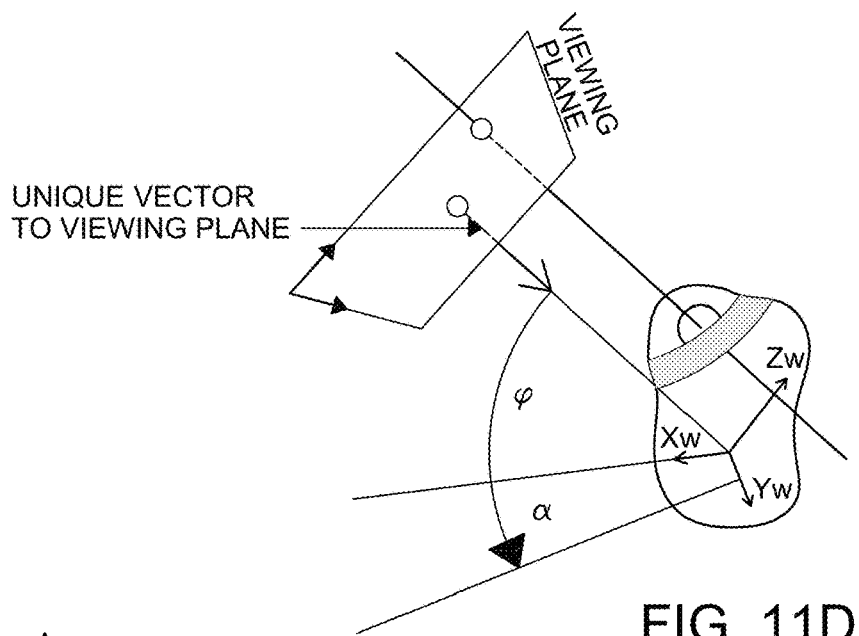
Figure 11E:
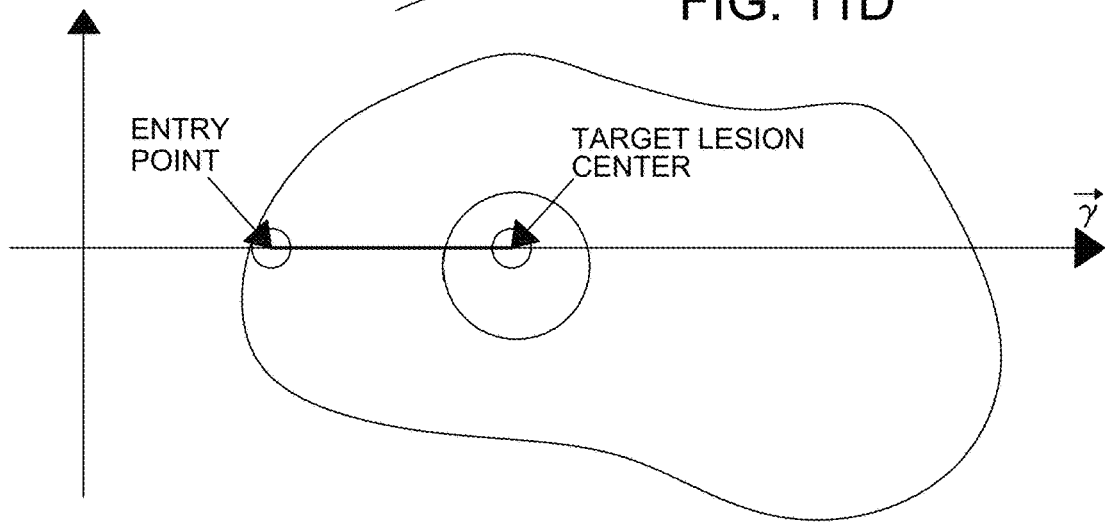
Figure 11F:
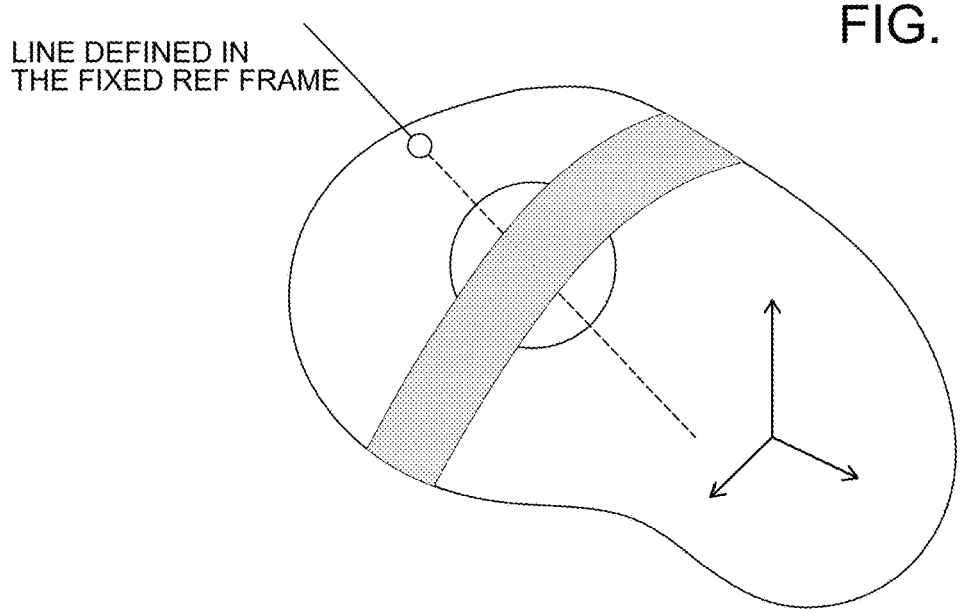

Referring now to FIG. 10, Illustrated here is a more detailed representation of the exemplary ablation probe assembly 500. The exemplary probe 500 comprises a cooling tube 502 and cable assembly 504 connected to a probe handle assembly 506. The probe handle 506 is connected to an antenna portion 508 via a cooled probe cannula 510. The region between the cooled probe cannula 510 and the antenna portion 508 comprises a stick portion 512 and a plug portion 514. The stick portion 512 is designed to attain and maintain a temperature accommodating adherence of a tissue region onto its surface. The plug portion 514 is designed to prevent a reduction in temperature resulting from the cooled probe cannula 510 and the stick portion 512 from affecting the temperature within the antenna portion 508. The ablation zone 516 is the energy pattern emitted by the antenna portion 508 for this single probe. As a non-limiting example, software of the present disclosure may determine the optimal placement and energy emitted by each probe to ensure no interference between probes.

With reference made to FIGS. 11A-11F, a method for determining a preferred pathway from a three-dimensional image of a region of the body is disclosed. As an example a method may comprise visualizing a three dimensional image of a region of the body with respect to a known reference frame, as shown in FIGS. 11A-11F. A method may comprise rotating the three dimensional image in the space in two dimensional spaces and obtaining vector information of a viewing plane, as shown in FIGS. 11A-11f. Methods may comprise determining a select body orientation to provide line-of-sight of a target location, obtaining spatial information of the target location with respect to the viewing plane, and/or determining a line in space based on at least the viewing plane and the spatial information of the target location defined with respect to the viewing plane. The line in space may represent at least a portion of the preferred pathway. Methods may further comprise determining a fiducial point that is associated with the line in space. The fiducial point may be determined based on automated feature recognition. The fiducial point may be an end point of the preferred pathway. The fiducial point may be an entry point on the external surface of the portion of the body being treated. As an example, the fiducial point may be determined using one or more of the following steps: visualizing a plane perpendicular to the initial viewing plane having the line in space represent the x-axis; and selecting on the line in space, an end point, while visualizing an imaging plane containing the line in space. Methods of determining the fiducial point may comprise selecting on the line in space, an entry point on the external surface of the body being treated, while visualizing an imaging plane containing the line in space. Other methods may be used.

A method for navigating a probe to a location within a body of a patient, the method comprising the steps of: visualizing a three-dimensional image of a region of a body of a patient; receiving a selection of a target location within said three-dimensional image of a region of a patient's body; determining and visualizing a preferred pathway for the probe to follow from an external entry point on the patient's body to the target location; registering the three-dimensional image to the current actual position of the corresponding region of the patient's body; registering the current actual position of the probe to the three-dimensional image and the current actual position of the patient's body; visualizing the preferred pathway for the probe simultaneously with an indication of the current actual position of the probe in real time such that the simultaneous visualizations enables a user to align the current actual position of the probe with the preferred pathway; and updating and visualizing an indication of the current actual position of the probe in real time as the probe is advanced to the target location.

The present disclosure relates to a method and associated system for guided navigation of one or more probes to locations within a body of a patient. The present disclosure is also directed to a method of and associated system for determining an accurate three-dimensional model of a tumor and its surrounding environment, inclusive of anatomical structure, as well as a means for automatically calculating the number of energy radiating probes and their respective positioning/trajectory specifics within the tumor(s) to ensure no destructive interference of the radiating energy in the patient and the complete eradication of the targeted cancerous cells. To achieve optimal trajectories for each probe utilized to ensure complete tumor destruction, the methodology of the present disclosure includes predictive analytics which account for the effects of tissue shrinkage due to electro-magnetic radiation exposure. In addition, the methodology of the present disclosure includes a means for accounting for anatomical shifting between initial scans and procedures as well as accounting for any phase-cancellation effects of using multiple microwave ablation probes.

The present disclosure also relates to a method for the three-dimensional modeling of tumors and the ablation thereof, and more particularly to a method and associated system for the three-dimensional modeling of tumors and surrounding tissue, the analysis of the models and the precise and complete ablation of the tumors based upon information from the models and analysis, including tumor geometry, electro-magnetic wave phase interference, heat sinking anatomical features and critical anatomy, to determine the number of ablation probes to utilize, the energy radiated by each probe, as well as the optimal trajectories for each probe. To achieve optimal trajectories for each probe utilized to ensure complete tumor destruction, the methodology of the present disclosure includes predictive analytics which account for the effects of tissue shrinkage due to electro-magnetic radiation exposure, for example, microwave radiation.

The present disclosure provides a means for mapping the electro-magnetic radiation distribution around the energy radiating probe, accounting for any heat sinking effects caused by near anatomical structures, providing predictive insights for positioning/tracking of any and all necessary energy radiating probes.

The present disclosure provides a means for the efficient and effective eradication of tumors as well as other undesirable tissue. The present disclosure may be utilized in conjunction with existing technology to provide truly accurate irradiation treatment.

The present disclosure may be utilized in conjunction with any type of probe. For example, the probe may be configured to emit RF energy, microwave energy, ultrasound energy, light energy and an electric field capable of causing irreversible electroporation. Non-energy emitting probes may also be utilized in accordance with the present disclosure.

The present disclosure comprises methods of determining an accurate three-dimensional model of the tumor and its surrounding environment, as well as a means for automatically calculating the number of and positioning/trajectory of the energy radiating probes within the tumor(s) to ensure no destructive interference of the radiating energy and the complete eradication of the cancerous cells. In addition, any method should preferably include predictive analytics which account for the effects of tissue shrinkage due to electromagnetic radiation exposure, for example, microwave radiation. In addition, the method may preferably include automatically guiding and positioning of the probes as well as a means for accounting for anatomical shifting.

Although shown and described in what is believed to be the most practical and preferred embodiments, it is apparent that departures from specific designs and methods described and shown will suggest themselves to those skilled in the art and may be used without departing from the spirit and scope of the disclosure. The present disclosure is not restricted to the particular constructions described and illustrated but should be constructed to cohere with all modifications that may fall within the scope of the appended claims.

What is claimed is:

1. A method for navigating a probe to a location within a body of a patient, the method comprising the steps of:
    visualizing a three-dimensional image of a region of the body of the patient;
    receiving a selection of a target location within said three-dimensional image of the region of the patient's body;
    determining and visualizing a preferred pathway for the probe to follow from an external entry point on the patient's body to the target location, the determining the preferred pathway step comprising:
        rotating the three-dimensional image;
        obtaining vector information of a viewing plane;
        determining a select body orientation of a select body to provide line-of-sight of the target location;
        obtaining spatial information of the target location with respect to the viewing plane; and
        determining a line in space based on at least the viewing plane and the spatial information of the target location defined with respect to the viewing plane, the line in space representing at least a portion of the preferred pathway,
    the preferred pathway being configured to minimize interference with radiating energy from one or more additional probes by automatically calculating one or more of the number of the additional probes, a respective positioning of the additional probes, or trajectories of the additional probes in a surrounding environment of the visualized preferred pathway;
    registering three-dimensional image to a current actual position of a corresponding region of the patient's body;
    registering the current actual position of the probe to the three-dimensional image and the current actual position of the patient's body;
    visualizing the preferred pathway for the probe simultaneously with an indication of the current actual position of the probe in real time such that the simultaneous visualization enables a user to align the current actual position of the probe with the preferred pathway;
    updating and visualizing the indication of the current actual position of the probe in real time as the probe is advanced to the target location; and
    visualizing a three-dimensional image of a target at the target location, with predictive analytics being used to account for tissue shrinkage of the target due to energy exposure.

2. The method of claim 1, further comprising calibrating the preferred pathway to compensate for shift of anatomical structures pre-operatively.

3. The method of claim 1, further comprising calibrating the preferred pathway to compensate for shift of anatomical structures intra-operatively.

4. The method of claim 1, further comprising updating the registration of the three-dimensional image of the region to the patient to compensate for shift of anatomical structures.

5. The method of claim 1, further comprising causing output of auditory or visual feedback to warn the user about information regarding proximity to the target location.

6. The method of claim 1, further comprising causing output of auditory or visual feedback to warn the user about information regarding proximity to anatomical structures to be avoided when navigating the probe.

7. The method of claim 1, wherein the probe comprises a needle, introducer, catheter, stylet, or sheath.

8. The method of claim 1, wherein the target location is at least a portion of a tumor.

9. The method of claim 1, wherein the receiving the selection of the target location is via interaction with a display device configured to output one or more of the visualizing steps.

10. The method of claim 1, further comprising visualizing, using ultrasound and in real time, the region of the body.

11. The method of claim 1, further comprising verifying, using an ultrasound device and in real time, that the preferred path does not intersect with anatomy to be avoided when navigating the probe.

12. The method of claim 1, further comprising verifying, using an ultrasound device and in real time, that the preferred path intersects with at least a portion of a tumor.

13. The method of claim 1, wherein the updating and visualizing the indication of the current actual position of the probe in real time as the probe is advanced to the target location is accomplished using at least an ultrasound device.

14. The method of claim 1, wherein the indication of the current actual position of the probe comprises the position of the probe in three-dimensional space.

15. The method of claim 1, wherein the indication of the current actual position of the probe comprises a projected extension of the probe in three-dimensional space.

16. The method of claim 1, wherein the three-dimensional image of the region of the body of the patient is based on one or more of magnetic resonance imaging (MRI), computer tomography (CT), or ultrasound.

17. A system for navigating a probe to a location within a body of a patient, the system comprising:
    a three-dimensional image of a region of the body of the patient;
    the probe, configured to be registered to the patient's body position in three-dimensional space;
    a registration system to register the three-dimensional image of the region of the body and a current actual position of the probe to a current actual position of the patient's body;
    an imaging device for capturing real-time images of the region of the body of the patient;

a computational machine for calculating a preferred pathway of the probe to a target location within the region of the body of the patient and in communication with the imaging device and the registration system, the computational machine being configured to calculate the preferred pathway by:
rotating the three-dimensional image,
obtaining vector information of a viewing plane,
determining a select body orientation of a select body to provide line-of-sight of the target location,
obtaining spatial information of the target location with respect to the viewing plane, and
determining a line in space based on at least the viewing plane and the spatial information of the target location defined with respect to the viewing plane,
the computational machine being configured to automatically calculate one or more of a number of additional probes, a respective positioning of the additional probes, or trajectories of the additional probes in a surrounding environment of the preferred pathway to minimize interference with radiating energy from one or more of the additional probes, the computational machine further calculating tissue shrinkage of a target at the target location from energy exposure using predictive analytics; and
a display for visualizing and providing updates of the real-time images from the imaging device, some characteristic of the current actual position of the probe in real-time as the probe is advanced to the target location, and the preferred pathway of the probe to the target location.

18. The system of claim 17, wherein the imaging device is configured to be registered to the patient's body using the registration system.

19. The system of claim 17, wherein the calculated preferred pathway is calibrated to compensate for shift of anatomical structures pre-operatively.

20. The system of claim 17, wherein the calculated preferred pathway is calibrated to compensate for shift of anatomical structures intra-operatively.

21. The system of claim 17, wherein the computational machine is further configured to cause output of an auditory or visual feedback to warn a user about information regarding proximity to the target location.

22. The system of claim 17, wherein the computational machine is further configured to cause output of an auditory or visual feedback to warn a user about information regarding proximity to anatomical structure to be avoided when navigating the probe.

23. The system of claim 17, wherein the probe comprises a needle, introducer, catheter, stylet, or sheath.

24. The system of claim 17, wherein the target location is at least a portion of a tumor.

25. The system of claim 17, wherein the imaging device comprises one or more of magnetic resonance imaging (MRI), computer tomography (CT), or ultrasound.

26. The system of claim 17, further comprising an augmented reality (AR) headset for visualizing some characteristic of the current actual position of the probe and the preferred pathway.

27. The system of claim 17, wherein some characteristic of the current actual position of the probe comprises a position of the probe in three-dimensional space.

28. The system of claim 17, wherein some characteristic of the current actual position of the probe comprises a projected extension of the probe in three-dimensional space.

29. A method for navigating a probe to a location within a body of a patient, the method comprising the steps of:
causing output of a three-dimensional image of a region of the body of the patient which includes a three-dimensional image of a target;
receiving, based on the three-dimensional image of the region of the body of the patient, a selection of a target location within said three-dimensional image of the region of the patient's body;
determining and visualizing a preferred pathway for the probe to follow from an external entry point on the patient's body to the target location, the determining the preferred pathway step comprising:
rotating the three-dimensional image;
obtaining vector information of a viewing plane;
determining a select body orientation of a select body to provide line-of-sight of the target location;
obtaining spatial information of the target location with respect to the viewing plane; and
determining a line in space based on at least the viewing plane and the spatial information of the target location defined with respect to the viewing plane, the line in space representing at least a portion of the preferred pathway,
the preferred pathway being configured to minimize interference with radiating energy from one or more additional probes by automatically calculating a number of the additional probes and one or more of a respective positioning or trajectories of the additional probes in a surrounding environment of the visualized preferred pathway;
causing output of the preferred pathway for the probe simultaneously with an indication of a current actual position of the probe such that the simultaneous output of the preferred pathway for the probe along with the indication of the current actual position of the probe enables a user to align a current actual position of the probe with the preferred pathway,
the three-dimensional image being registered to a current actual position of the corresponding region of the patient's body,
the current actual position of the probe being registered to the three-dimensional image and the current actual position of the patient's body;
updating and visualizing the indication of the current actual position of the probe in real time as the probe is advanced to the target location; and
visualizing the three-dimensional image of the target and using predictive analytics to account for tissue shrinkage of the target due to energy exposure.

30. The method of claim 29, further comprising calibrating the preferred pathway to compensate for shift of anatomical structures pre-operatively.

31. The method of claim 29, further comprising calibrating the preferred pathway to compensate for shift of anatomical structures intra-operatively.

32. The method of claim 29, further comprising updating the registration of the three-dimensional image to the patient to compensate for shift of anatomical structures.

33. The method of claim 29, further comprising causing output of an auditory or visual feedback to warn the user about information regarding proximity to the target location.

34. The method of claim 29, further comprising causing output of an auditory or visual feedback to warn the user about information regarding proximity to anatomical structures to be avoided when navigating the probe.

35. The method of claim 29, wherein the probe comprises a needle, introducer, catheter, stylet, or sheath.

36. The method of claim 29, wherein the target location is at least a portion of a tumor.

37. The method of claim 29, wherein the receiving the selection of the target location is via interaction with a display device configured to output one or more of the visualizing steps.

38. The method of claim 29, further comprising visualizing, using ultrasound and in real time, the region of the body.

39. The method of claim 29, further comprising verifying, using an ultrasound device and in real time, that the preferred path does not intersect with anatomy to be avoided when navigating the probe.

40. The method of claim 29, further comprising verifying, using an ultrasound device and in real time, that the preferred path intersects with at least a portion of a tumor.

41. The method of claim 29, wherein the updating and visualizing the indication of the current actual position of the probe in real time as the probe is advanced to the target location is accomplished using at least an ultrasound device.

42. The method of claim 29, wherein the indication of the current actual position of the probe comprises the position of the probe in three-dimensional space.

43. The method of claim 29, wherein the indication of the current actual position of the probe comprises a projected extension of the probe in three-dimensional space.

44. The method of claim 29, wherein the three-dimensional image of the region of the body of the patient is based on one or more of magnetic resonance imaging (MRI), computer tomography (CT), or ultrasound.

\* \* \* \* \*